United States Patent [19]

Koslo

[11] Patent Number: 4,980,159

[45] Date of Patent: Dec. 25, 1990

[54] PROCESSES AND COMPOSITIONS FOR THE TOPICAL APPLICATION OF β-ADRENERGIC AGONISTS FOR PILOMOTOR EFFECTS

[75] Inventor: Randy J. Koslo, East Windsor, N.J.

[73] Assignee: Bristol-Myers Squibb Company, New York, N.Y.

[21] Appl. No.: 355,565

[22] Filed: May 23, 1989

[51] Int. Cl.$^5$ .................... A61K 7/15; A61K 7/155
[52] U.S. Cl. .................................... 424/73; 8/161
[58] Field of Search ........................... 424/73; 8/161

[56] References Cited

U.S. PATENT DOCUMENTS 4,853,216  8/1989  Koslo et al. ................ 424/73

FOREIGN PATENT DOCUMENTS 1032482  6/1958  Fed. Rep. of Germany ........ 424/73

*Primary Examiner*—Merrell C. Cashion, Jr.
*Assistant Examiner*—Susan S. Rucker
*Attorney, Agent, or Firm*—Eliot S. Gerber; Henry T. Burke

[57] ABSTRACT

Processes and compositions for effecting pilomotor retraction of the hair on a hair-bearing skin area by the topical application of a β-adrenergic agonist.

14 Claims, No Drawings

PROCESSES AND COMPOSITIONS FOR THE TOPICAL APPLICATION OF β-ADRENERGIC AGONISTS FOR PILOMOTOR EFFECTS

BACKGROUND OF THE INVENTION

1. Field of The Invention

This invention relates to processes and compositions for the topical application of β-adrenergic receptor agonists to effect retraction of the hair in a hair-bearing skin area. More particularly, it relates to processes for the treatment of hair-bearing skin areas in humans for the purpose of retracting the hair in the area thereby to make the area appear and feel smooth.

2. Description of The Related Art

The processes of this invention have a wide variety of applications, for example, in conjunction with depilatory waxes, chemical depilatories, bleach creams and the like. They have particular application in conjunction with shaving processes and compositions. To simplify the description of the invention, emphasis will be placed on its application to such shaving processes and compositions as exemplary of the broader concept of the invention.

The compositions used in the processes of this invention can be applied to any of a variety of hair-bearing skin areas. When used in conjunction with the shaving processes and compositions, for example, the compositions used in the invention may be applied to the legs, axillary vaults, facial skin, etc. of the subject. When used in conjunction with bleach creams, the compositions may also be applied to hair-bearing areas of the head and extremities thereby making the bleaching process appear more effective.

One of the criteria of a "good" shave is that, after the shave, the area should appear and feel smooth. This can be achieved by a so-called close shave in which the razor, be it manual or machine, cuts the hair as close as possible to the skin. To that end, it has been proposed to apply a piloerection agent to the area to be shaved prior to the actual shaving process. The erection of the hair facilitates the achievement of a close shave.

Sympathomimetic agents causing piloerection are disclosed in copending and commonly assigned application, Ser. No. 33987, filed Apr. 2, 1987 U.S. Pat. No. 4,853,216, which describes and claims the use of compositions containing α-adrenergic receptor agonists to elicit a pilomotor response of hair erection.

Another method for achieving a smooth appearance and feel is to cause the hair to retract, i.e., recede into the skin, after the shaving process is complete. It has now been discovered that topical application of β-adrenergic receptor agonists to the hair-bearing area will surprisingly elicit a pilomotor response which will cause the hair to retract.

As is known in the pharmacology art, adrenergic receptors are two general types. There are α-adrenergic receptors and β-adrenergic receptors. For example, norepinephrine is a classic α-adrenergic receptor stimulator while isoproterenol is a classic β-adrenergic receptor stimulator. Such compounds are also known as agonists. Compounds having the opposite effect are known as antagonists. The compounds utilized in this invention are β-adrenergic receptor agonists.

It is surprising to find that β-adrenergic receptor agonists will effect a pilomotor response of relaxation of the arrectores pilorum muscles causing the hair in the hair-bearing area to retract. As is evident from the above identified copending application, it was the original understanding of the inventors thereof that all sympathomimetic agents including α- and β-receptor agonists caused pilomotor erection of the hair ———— not retraction. So far as is known, there have been no previous teachings or suggestions of the use of β-adrenergic receptor agonists to effect pilomotor retraction of hair. U.S. Pat. No. 4,038,417 describes the topical application of such compounds for the treatment of psoriasis.

Summary of The Invention

Any non-toxic β-adrenergic agonist that can be formulated into a composition for topical application can be employed in this invention to achieve the desired results. Typically, these compounds are derivatives of phenylethylamine with one or two hydroxyl groups on the phenyl ring. The preferred compounds of the invention are isoproterenol, metaproterenol, dobutamine, ethylnorepinephrine, isoetharine, terbutaline, ritodrine, prenalterol and albuterol (salbutamol). Of these, metaproterenol is the most preferred because it is readily and economically available and is compatible with the usual excipients utilized in topical compositions.

The β-adrenergic receptor agonists employed in this invention may be formulated with a wide variety of other ingredients to form lotions, creams, foams and other vehicles containing an amount of the selected β-adrenergic receptor agonist which is effective to elicit a hair retraction response together with at least one topically acceptable excipient. However, by far the most preferred compositions are liquid compositions, typically solutions having about the same viscosity as water. Such compositions can be readily applied to the hair-bearing area by hand, although various forms of applicators such as sponges, roll-ons and aerosols may also be employed. These compositions are preferred over creams, lotions and the like because they can be applied to the skin without extensive rubbing, and they leave little or no residue.

As indicated above, the compositions will be applied to the skin after shaving to enhance the appearance and feel of the treated area. In each instance, the β-receptor agonists will be present in sufficient concentration to elicit a muscle relaxation and hair retraction response in the hair-bearing area. This concentration may vary somewhat for different agonists. Generally, however, the β-receptor agonist, or mixture of β-receptor agonists, will be present in the range of from about 0.1% to about 10% by weight based on the total weight of the composition in which it is contained. The concentration may vary somewhat from this range without adverse effect, although at concentrations appreciably below 0.1% there may not be sufficient retraction to achieve the desired feel and appearance. It is rarely necessary to utilize concentrations above 10%. Therefore, such compositions are usually uneconomical. The preferred concentration is from about 0.2% to 2.0% on the same weight basis.

The after-shave, aqueous, liquid compositions of this invention are novel. They are characterized principally by the presence of a sufficient amount of a water miscible alkanol such as ethanol or isopropanol in the aqueous carrier vehicle to insure rapid evaporation of the vehicle from the skin. Such compositions will normally contain the above defined quantities of β- adrenergic agonists, about 3% to 6% by weight of the selected alcohol and at least about 60% water. The balance of the composition will contain one or more of the fragrances, preservatives or other ingredients mentioned below.

The amount of alcohol in the compositions is selected to enhance the evaporation rate. More alcohol can be employed if desired, but the addition of more alcohol will normally increase the costs of the product without an appreciable improvement in the evaporation rate.

Normally, it will be preferred to employ more than 60% by weight water to reduce the costs of the product. In fact, many compositions within the scope of the invention will contain 80%, or an even higher percentage of water by weight.

Description of The Preferred Embodiments

When used in the compositions of this invention, the nature of the ingredients other than the active agents can vary considerably. As mentioned above, the β-receptor agonists will usually be distributed in a liquid carrier. By way of illustration, such liquid carriers may comprise: a) water or any aqueous solution containing organic or inorganic materials such as sodium chloride or an alkanol; b) organic solvents such as ethyl or isopropyl alcohol or a glycol such as propylene glycol. The pH is normally from about 6 to 8.

Additionally, the compositions may contain one or more ingredients to modify or enhance their texture, appearance, scent performance or stability. Illustrative additives to the compositions include:

1. Lubricants, such as silicones or isopropyl myristate,
2. Astringents such as lactic acid or zinc phenolsulfonate,
3. Fragrances such as bay oil, rose water, orange oil, myrrh or musk,
4. Medicinals and antiseptics such as menthol and camphor,
5. Emollients such as glycerols and sorbitols, and
6. Preservatives such as ascorbic acid, parahydroxybenzoic acid esters and tocopherols.

For additional ingredients that may be included in the compositions employed in this invention, attention is directed to the following citation which is incorporated herein by way of reference: Bell, S. A. 1972, Preshave and Aftershave Preparations pp. 13–37 in M. S. Bulsam and E. Sagarin, editors, Volume 2, Cosmetics: Science and Technology. Wiley Interscience, New York.

Those skilled in the art will recognize that the preferred β-receptor agonists of this invention are basic amines. Accordingly, they may be employed as the free amine or as any of a variety of inorganic and organic acid addition salts with pharmaceutically acceptable organic and inorganic acids such as hydrochloric, sulfuric, citric or malic acids. The amines also contain active hydrogens on the hydroxyl and the amine moieties so that the parent compounds can be converted into esters or amines to produce derivatives retaining the β-receptor adrenergic activity of the parent compounds. All such compounds are included within the scope of the invention.

The following examples are given by way of illustration only and are not to be construed as limitations of this invention many apparent variations of which are possible without departing from its spirit or scope.

EXAMPLE 1

The following topical compositions, all of which have pilomotor relaxation activity when applied to human skin-bearing areas are prepared by mixing the ingredients in the percent by weight indicated. All components are highly purified and generally are either N.F. or U.S.P.

| Ingredient | % w/w |
|---|---|
| A. AFTER-SHAVE LIQUID SOLUTION | |
| Isoproterenol | 2.0 |
| Propylene glycol | 3.0 |
| Isopropyl alcohol | 3.0 |
| Methyl parahydroxy benzoate | 0.1 |
| Propyl parahydroxybenzoate | 0.1 |
| Water | 91.8 |
| B. AFTER-SHAVE LIQUID SOLUTION | |
| Metaproterenol | 10.0 |
| Ethyl alcohol | 4.0 |
| Menthol | 0.1 |
| Camphor | 0.1 |
| Isopropyl myristate | 19.0 |
| Rose water | 66.8 |
| C. CREAM | |
| Salbutamol | 0.3 |
| Paraffin oil | 30.0 |
| Wool fat, anhydrous | 3.0 |
| Stearic acid | 12.0 |
| Isopropyl myristate | 3.0 |
| Triethaholamine | 1.5 |
| Methyl parahydroxy benzoate | 0.02 |
| Propyl parahydroxy benzoate | 0.02 |
| Musk oil | 0.10 |
| Water | 50.06 |
| D. LOTION | |
| Metaproterenol | 0.5 |
| Di-isopropyl adipate | 10.0 |
| Ethanol | 60.0 |
| Boric acid | 1.0 |
| Orange oil | 0.5 |
| Water | 28.0 |

EXAMPLE 2

Volunteers were pretreated by applying 30% SD 40 Alcohol (controls) or a 1% solution of metaproterenol in 30% SD 40 alcohol to the face. The volunteers then shaved with an electric razor. After each shave, the beard shavings were removed from the razor and weighed. Beard weight was used as the measure of productivity. Pretreatment with metaproterenol decreased shaving productivity to 82±10% of the control, thus indicating hair retraction in the shaved area.

When the experiment is repeated, using the α-adrenergic receptor agonist, phenylephrine hydrochloride as a piloerection agent at a concentration of 1% by weight in a 2:1 ethanol/water solution, the shaving productivity increases compared to control. This further confirms the original observation that metaproterenol is an active agent and is not acting in a nonspecific way, since metaproterenol and phenylephrine have opposite effects.

What is claimed is:

1. A process for effecting a pilomotor retraction of the hair in a hair-bearing skin area which comprises applying topically to said area an amount of a β-adrenergic agonist which is sufficient to effect such retraction.

2. The process of claim 1 wherein said β-adrenergic agonist is contained in a post-shave preparation.

3. The process of claim 1 or 2 wherein said β-adrenergic agonist is selected from the group consisting of isoproterenol, metaproterenol, dobutamine, ethylnorepinephrine, isoetharine, terbutaline, ritodrine, albuterol and prenalterol.

4. The process of claim 1 or 2 wherein said β-adrenergic agonist is metaproterenol.

5. The process of claim 1 or 2 wherein the β-adrenergic agonist is applied in a composition which contains from about 0.1% to about 10% by weight of a β-adrenergic agonist, based on the total weight of the composition together with at least one topically acceptable excipient.

6. The process of claim 1 or 2 wherein the β-adrenergic agonist is applied in a composition which contains from about 0.2% to 2% by weight of a β-adrenergic agonist, based on the total weight of the composition together with at least one topically acceptable excipient.

7. In a shaving process involving the use of a razor to cut hair from a hair-bearing area of the skin, the improvement which comprises topically applying to said area, after the shaving process is complete, an amount of a β-adrenergic agonist which is effective to elicit a hair-retraction response in the area where it is applied.

8. The process of claim 7 wherein said β-adrenergic agonist is selected from the group consisting of isoproterenol, metaproterenol, dobutamine, ethylnorepinephrine, isoetharine, terbutaline ritodrine, albuterol and prenalterol.

9. The process of claim 8 wherein said β-adrenergic agonist is metaproterenol.

10. The process of claim 7, 8 or 9 wherein the β-adrenergic agent is applied in a composition which contains from about 0.1% to about 10% by weight of a β-adrenergic agonist, based on the total weight of the composition together with at least one topically acceptable excipient.

11. A process as in claim 7, 8 or 9 wherein the β-adrenergic agent is applied in a composition which contains from about 0.2% to 2% by weight of a β-adrenergic agonist, based on the total weight of the composition together with at least one topically acceptable excipient.

12. An after-shave composition comprising 0.1% to 10% of a β-adrenergic agonist, 3% to 6% of ethanol, isopropanol or a mixture thereof and at least 60% water, all percentages being by weight based on the total weight of the composition.

13. The after-shave composition of claim 12 containing from 0.2% to 2% by weight of a β-adrenergic agonist, based on the total weight of the composition.

14. The after-shave composition of claim 12 or 13 wherein said β-adrenergic agonist is selected from the group consisting of isoproterenol, metaproterenol, dobutamine, ethylnorepinephrine, isoetharine, terbutaline, ritodrine, albuterol and prenalterol.

* * * * *